(12) United States Patent
Mizusawa et al.

(10) Patent No.: US 12,049,469 B2
(45) Date of Patent: Jul. 30, 2024

(54) COMPOUND AND STRUCTURAL BODY FOR DETECTING HYDROGEN SULFIDE

(71) Applicant: CANON KABUSHIKI KAISHA, Tokyo (JP)

(72) Inventors: Keigo Mizusawa, Kanagawa (JP); Takeshi Yamamoto, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 255 days.

(21) Appl. No.: 17/529,143

(22) Filed: Nov. 17, 2021

(65) Prior Publication Data

US 2022/0162226 A1     May 26, 2022

(30) Foreign Application Priority Data

Nov. 26, 2020 (JP) .................................. 2020-196001

(51) Int. Cl.
| | | |
|---|---|---|
| *C07D 493/10* | (2006.01) | |
| *G01N 21/64* | (2006.01) | |
| *G01N 33/49* | (2006.01) | |
| *G01N 33/52* | (2006.01) | |

(52) U.S. Cl.
CPC ....... *C07D 493/10* (2013.01); *G01N 21/6428* (2013.01); *G01N 33/4925* (2013.01); *G01N 33/52* (2013.01); *G01N 2021/6439* (2013.01)

(58) Field of Classification Search
CPC .................................................. C07D 493/10
See application file for complete search history.

(56) References Cited

U.S. PATENT DOCUMENTS

| | | | |
|---|---|---|---|
| 6,552,199 B1 | 4/2003 | Daltrozzo et al. | |
| 2012/0329085 A1 | 12/2012 | Chang | |
| 2018/0074068 A1 | 3/2018 | Xian | |

FOREIGN PATENT DOCUMENTS

| | | |
|---|---|---|
| CN | 103937491 A | 7/2014 |
| CN | 104974169 A | 10/2015 |
| CN | 106967038 A | 7/2017 |
| CN | 110734450 A | 1/2020 |
| CN | 110950877 A | 4/2020 |
| CN | 111825692 A | 10/2020 |
| WO | 97/49769 A1 | 12/1997 |
| WO | 00/58406 A1 | 10/2000 |
| WO | 2012144654 A1 | 10/2012 |
| WO | 2019231503 A1 | 12/2019 |

OTHER PUBLICATIONS

Huang, K., et a., "A novel FRET-based ratiometric fluorescent probe for highly sensitive detection of hydrogen sulfide", RSC Adv., 2015, pp. 17797-17801, vol. 5.

Yoon, H.J., et al., "Synthesis and evaluation of self-calibrating ratiometric viscosity sensors", Org Biomol Chem, May 7, 2011, pp. 3530-3540, vol. 9, No. 9.

Iyori, Y., et al., "Nickel-Catalyzed Reductive Defunctionalization of Esters in the absence of an External Reductant: Activation of C—O Bonds", Chem. Commun., 2019.

Liu, C., et al., Reaction Based Fluorescent Probes for Hydrogen Sulfide, Org Lett., Apr. 20, 2012, pp. 2184-2187, vol. 14, No. 8.

*Primary Examiner* — Shawquia Jackson

(74) *Attorney, Agent, or Firm* — Canon U.S.A., Inc. I.P. Division

(57) ABSTRACT

A compound in which a xanthene colorant is bonded to an optical absorber (Dye) with optical absorption in the wavelength range of 350 to 700 nm.

20 Claims, 1 Drawing Sheet

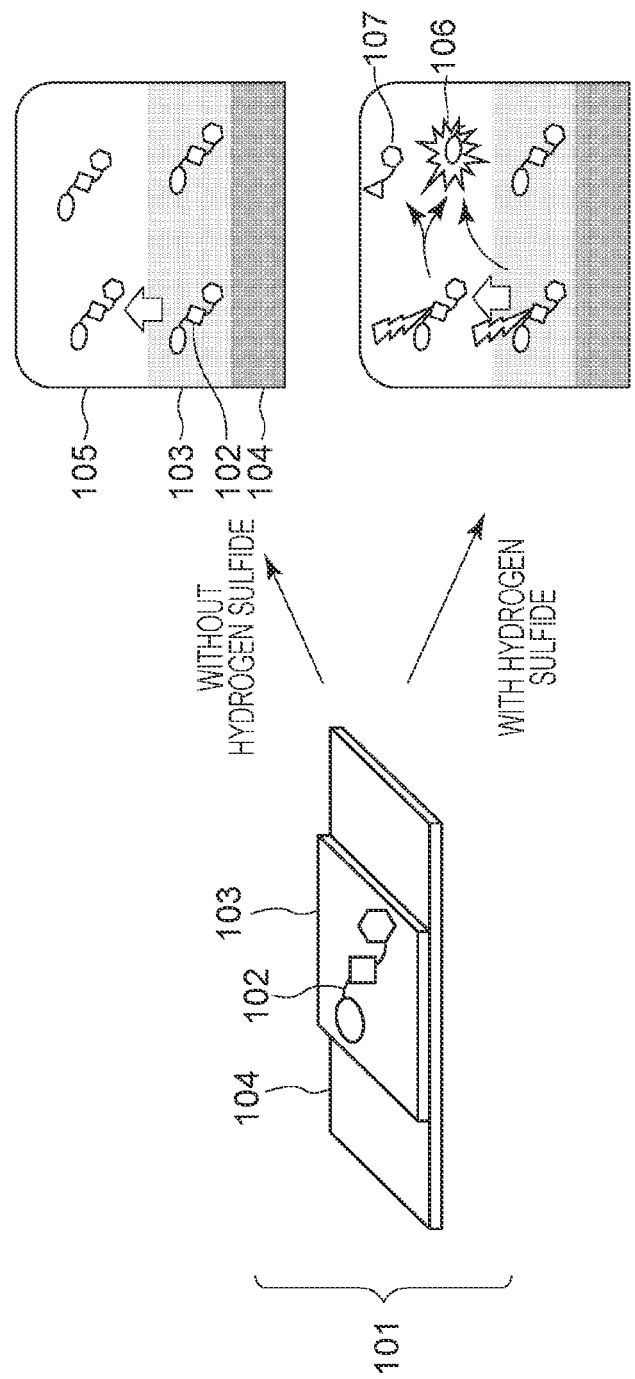

COMPOUND AND STRUCTURAL BODY FOR DETECTING HYDROGEN SULFIDE

BACKGROUND OF THE INVENTION

Field of the Invention

The present disclosure relates to a novel compound and a structural body for detecting hydrogen sulfide.

Description of the Related Art

For the detection of hydrogen sulfide in an aqueous specimen, there is a demand for not only the detection of hydrogen sulfide itself but also the detection of hydrogen sulfide as a product of an enzymatic reaction. Examples include examination of soil and water in factories, industrial waste treatment plants, sewage treatment plants, and surrounding areas; dynamic analysis of living bodies and living cells as biologically active substances; breath tests; and detection and quantitative measurement of cysteine, methionine, homocysteine, and the like in body fluids. Cysteine, methionine, homocysteine, and the like can be detected from the amount of hydrogen sulfide generated by a reaction with a specific enzyme, such as a lyase. Such a case requires detection and quantitative measurement of hydrogen sulfide.

A functional colorant that causes a detectable color change (absorption or light emission) in the presence of hydrogen sulfide may be used to detect hydrogen sulfide.

The functional colorant may be o-methylfluorescein bonded to a methyl 2-cyano-3-phenyl acrylate derivative that reacts with hydrogen sulfide. This compound is known to react with hydrogen sulfide and fluoresce in a visible region around 520 nm (Org Lett. 2012, 14, 2184-2187, hereinafter referred to as Non Patent Literature 1).

SUMMARY OF THE INVENTION

To detect hydrogen sulfide and metabolites in an aqueous specimen, such as a biological sample, the present inventors have examined whether the compound disclosed as a detection material in Non Patent Literature 1 can detect hydrogen sulfide in neutral phosphate-buffered saline. It was found that a precipitate or aggregate of the detection material is formed in the solution and thereby lowers reactivity with hydrogen sulfide and makes it difficult to detect hydrogen sulfide with high sensitivity. Thus, the present inventors have found that a method for increasing the water solubility of a detection material is required to increase the detection sensitivity of hydrogen sulfide.

The present inventors have found that fluorescein with a hydroxy group as a hydrophilic group has higher water solubility than o-methyl fluorescein. It was also found that the detection of hydrogen sulfide was difficult with fluorescein bonded to a methyl 2-cyano-3-phenyl acrylate derivative, which always fluoresces regardless of the presence or absence of hydrogen sulfide.

The present disclosure provides a novel material for highly sensitive detection of hydrogen sulfide in an aqueous specimen, such as a biological sample.

A compound according to the present disclosure is represented by the formula 1:

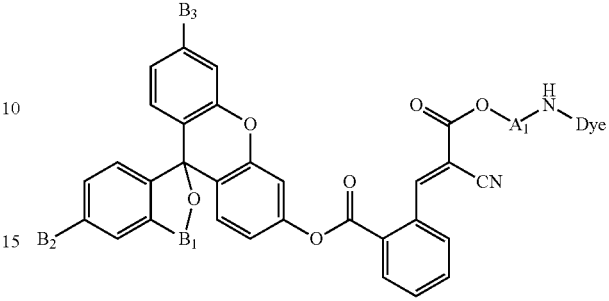

(formula 1)

In the formula 1,

Dye denotes an optical absorber with optical absorption in a wavelength range of 350 to 700 nm and with a highest molecular absorption coefficient of $10^4$ $M^{-1}$ $cm^{-1}$ or more, $A_1$ denotes a substituted or unsubstituted alkylene or alkoxy group having 3 to 12 carbon atoms, $B_1$ denotes a member selected the group consisting of —C(=O)—, —S(=O)$_2$—, and —CH$_2$—, $B_2$ denotes a member selected the group consisting of —H, —NHC(=S)NH—(CH$_2$CH$_2$O)$_n$—CH$_3$, and —NHC(=S) amino acids, wherein n denotes an integer in the range of 1 to 25, and $B_3$ denotes a member selected the group consisting of —OH, —NH$_2$, —NHCH$_3$, —NHCH$_2$CH$_3$, —N(CH$_3$)$_2$, and —N(CH$_2$CH$_3$)$_2$.

Further features of the present disclosure will become apparent from the following description of exemplary embodiments with reference to the attached drawing.

BRIEF DESCRIPTION OF THE DRAWINGS

FIGURE is a schematic view of an example of a structural body for detecting hydrogen sulfide according to the present embodiment.

DESCRIPTION OF THE EMBODIMENTS

Although some embodiments of the present disclosure are described below, the present disclosure is not limited to these embodiments.

First Embodiment

Compound

A compound according to the present embodiment is represented by the formula 1:

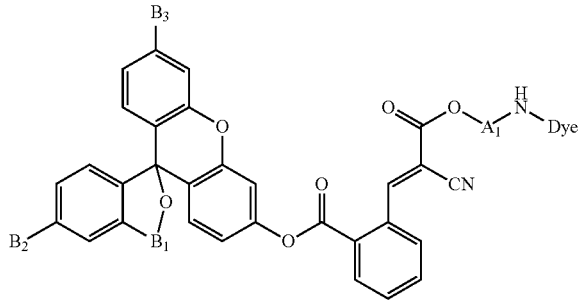

(formula 1)

The formula 1 is described in detail below.

Dye

Dye in the formula 1 denotes an optical absorber with optical absorption in the wavelength range of 350 to 700 nm and with a highest molecular absorption coefficient of $10^4$ $M^{-1}$ $cm^{-1}$ or more. Furthermore, the Dye according to the present embodiment preferably has optical absorption in the wavelength range of 365 to 650 nm.

The Dye according to the present embodiment may be a dye, a pigment, a fluorescent material, a non-fluorescent material, a colorant, gold nanoparticles, a gold colloid, or silver nanoparticles, each having an ionic or nonionic functional group.

For example, when the Dye according to the present embodiment is a colorant, the Dye may be an azo colorant, a xanthene colorant, a coumarin colorant, a triarylmethane colorant, or ethidium bromide. The Dye according to the present embodiment can be at least a member selected the group consisting of azo colorants, xanthene colorants, and coumarin colorants, particularly an azo colorant with a function as a quencher.

The Dye in the formula 1 can be represented by the formula 2:

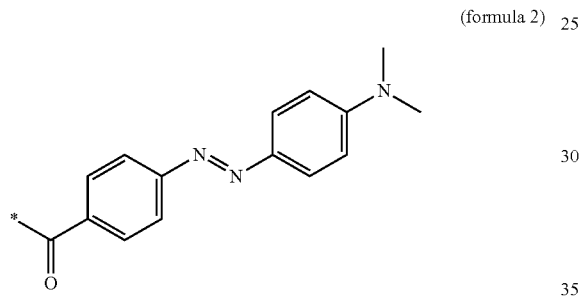

(formula 2)

* in the formula 2 denotes the position of N of NH in the formula 1.

Specific examples of the structure of the Dye in the formula 1 that can be used in the present embodiment include the following formulae (d1) to (d18). * denotes the position of N of NH in the formula 1. In other words, * denotes a bonding arm bonded to N of —NH in the formula 1. * hereinafter denotes the same.

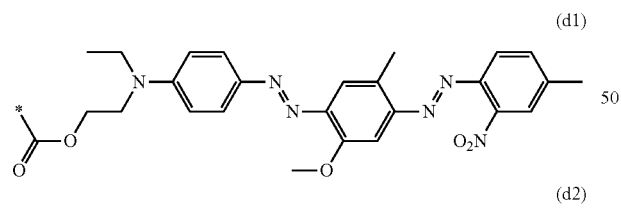

(d1)

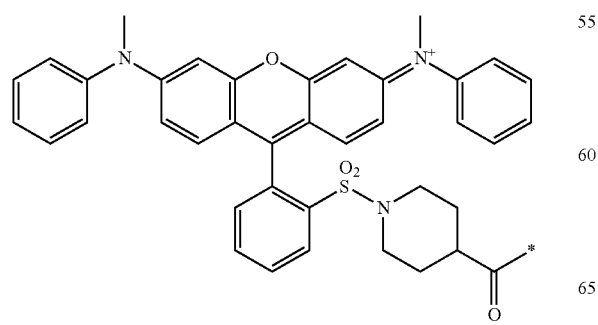

(d2)

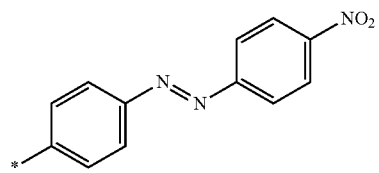

(d3)

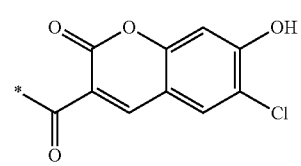

(d4)

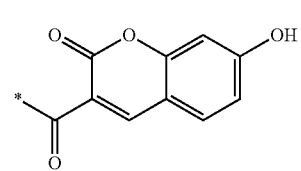

(d5)

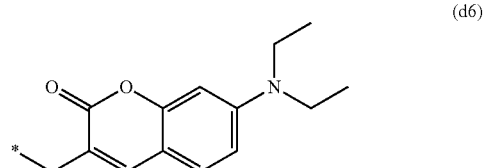

(d6)

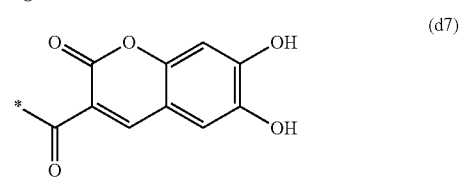

(d7)

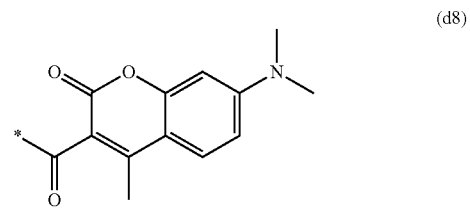

(d8)

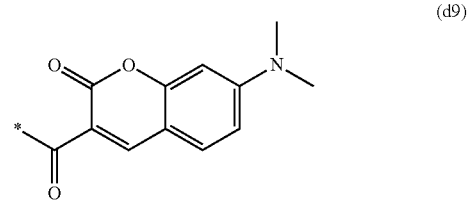

(d9)

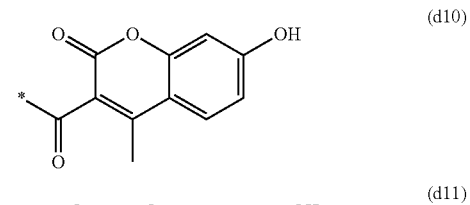

(d10)

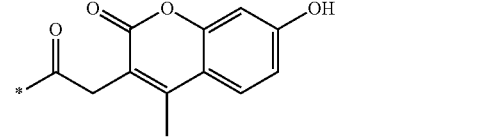

(d11)

-continued

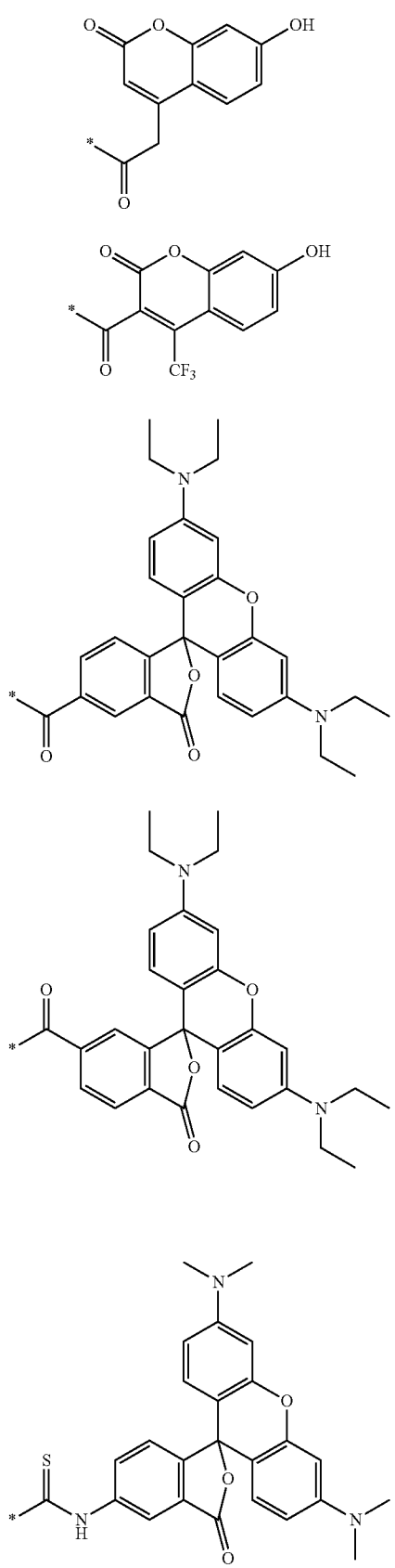

(d12)

(d13)

(d14)

(d15)

(d16)

(d17)

(d18)

A₁

A₁ in the present embodiment denotes a substituted or unsubstituted alkylene or alkoxy group having 3 to 12 carbon atoms. This is because a shorter distance between a xanthene colorant and the Dye can result in higher energy transfer efficiency therebetween and larger quenching. A₁ in the present embodiment can be an unsubstituted alkylene group having 3 carbon atoms.

B₁

B₁ in the present embodiment denotes a member selected the group consisting of —C(═O)—, —S(═O)₂—, and —CH₂—. In an aqueous solution with a neutral pH, such as under physiological conditions, a ring structure opens and changes into a water-soluble functional group, such as —CO₂⁻, —SO₃⁻, or —CH₂OH. This can increase the water solubility of the compound represented by the formula 1 and prevent a decrease in detection sensitivity due to precipitation or aggregation. To increase the water solubility, B₁ in the present embodiment can denote —C(═O)—.

B₂

B₂ in the present embodiment denotes a member selected the group consisting of —H, —NHC(═S)NH—(CH₂CH₂O)ₙ—CH₃, and —NHC(═S) amino acids, wherein n denotes an integer in the range of 1 to 25. These are water-soluble functional groups and can increase the water solubility of the compound and prevent a decrease in detection sensitivity due to precipitation or aggregation. To increase the water solubility, B₂ in the present embodiment can denote —H, —NHC(═S)NH—(CH₂CH₂O)ₙ—CH₃, or —NHC(═S)NH—CHR—COOH, wherein R denotes an amino acid side chain, and n can range from 4 to 22. When B₂ in the present embodiment denotes —NHC(═S)NH—CH₂—COOH, the amino acid of the —NHC(═S) amino acids is glycine.

B₃

B₃ in the present embodiment denotes a member selected the group consisting of —OH, —NH₂, —NHCH₃, —NHCH₂CH₃, —N(CH₃)₂, and —N(CH₂CH₃)₂. B₃ in the present embodiment can denote —OH or —NH₂, particularly —OH. These are water-soluble functional groups and can increase the water solubility of the compound and prevent a decrease in detection sensitivity due to precipitation or aggregation. To increase the water solubility, $B_3$ in the present embodiment can denote —OH or —$NH_2$, particularly —OH.

Operational Advantages

As described above, the compound according to the present embodiment contains a large amount of water-soluble functional group and therefore has high water solubility.

As shown in the formula 1, a 2-cyano-3-phenyl acrylate derivative is used as a linker to link the xanthene colorant to the Dye. Thus, a fluorescence resonance energy transfer (FRET) phenomenon occurs between the xanthene colorant and the Dye. Consequently, irradiation with excitation light of a specific wavelength causes quenching or fluorescence at two different wavelengths different from the specific wavelength. The 2-cyano-3-phenyl acrylate derivative reacts with hydrogen sulfide to separate the xanthene colorant from the Dye. The separation prevents the FRET phenomenon and increases fluorescence intensity or changes the fluorescence intensity ratio of two different wavelengths. Thus, the amount of hydrogen sulfide can be estimated by the amount or ratio of an increase in fluorescence intensity or by the amount of change in intensity ratio due to the reaction with hydrogen sulfide. For energy transfer in the FRET phenomenon, the xanthene colorant can act as a donor, and the Dye can act as an acceptor. Alternatively, the xanthene colorant can act as an acceptor, and the Dye can act as a donor. Non Patent Literature 1 discloses a method utilizing Michael addition of hydrogen sulfide to a vinyl carbon of the methyl 2-cyano-3-phenyl acrylate derivative as an initiation reaction and then cleavage of an ester bond by an intramolecular cyclization reaction to cause decomposition.

A small amount of hydrogen sulfide separates a small amount of xanthene colorant from the Dye. By contrast, a large amount of hydrogen sulfide separates a large amount of xanthene colorant from the Dye. Thus, the amount of hydrogen sulfide can also be estimated by measuring the amount of separated xanthene colorant or Dye. The amount of hydrogen sulfide can also be estimated by measuring the fluorescence or absorbance of the xanthene colorant, the Dye, or both the xanthene colorant and the Dye. Thus, the mechanism for detecting hydrogen sulfide in a compound according to each embodiment is different from a known detection mechanism using only a xanthene colorant structure as described in Non Patent Literature 1 and is less likely to be affected by precipitation or aggregation.

Thus, the compound according to the present embodiment can detect hydrogen sulfide in an aqueous specimen, such as a biological sample, with high sensitivity.

Biological Sample

A biological sample in the present embodiment may be urine, blood, sweat, tears, saliva, or mucus, or a liquid sample thereof, or a diluted or concentrated liquid thereof containing an increased or decreased amount of water. With respect to an analyte to be detected in these samples, the amount and concentration of a metabolite to be detected in a biological sample can be measured by bringing the biological sample into contact with an enzyme and hydrogen sulfide detection apparatus.

Analyte to be Detected

An analyte to be detected in the present embodiment may be a biomarker related to a disease in the living body, physical conditions, the degree of stress on the living body, or the like. An analyte to be detected according to an embodiment of the present disclosure may be, but is not limited to, hydrogen sulfide, methanethiol, cysteine, or homocysteine. The analyte to be detected can be contained in urine, blood, sweat, tears, saliva, or the like.

Use

The compound according to the present embodiment may be used in a structural body according to a second embodiment or may be used in another apparatus or measuring device. The apparatus or measuring device may be an automatic blood analyzer for clinical use, a simple test apparatus for medical use, a rapid diagnostic test apparatus, or a biochemical test apparatus. The apparatus or measuring device may also be, but is not limited to, a lateral flow test chip, a flow through test chip, a dipstick, a microfluidic chip, a microchemical chip, or a biochip.

Second Embodiment

Structural Body

A structural body according to the present embodiment includes a base material and the compound according to the first embodiment located on the base material.

Base Material

In the present embodiment, the base material may be a solid material and can have low reactivity with hydrogen sulfide. The base material in the present embodiment can be glass, ceramic, a silicon resin, paper made of cellulose or μ-fiber, felt, knit fabric, non-woven fabric, a porous material, or filter paper and can be a paper material in terms of availability.

The base material in the present embodiment may also be a glass on which a flow path or a circle is etched or a paper material on which a flow path or a circular frame is printed with a hydrophobic material. The hydrophobic material in the present embodiment may be, but is not limited to, at least one material selected from the group consisting of waxes, crayons, paraffin, SU-8, silicon, oil-based markers, poly(acrylic acid), acrylic lacquers, alkyl ketone dimers, polystyrene, octadecyltrichlorosilane, polydimethylsiloxane, polyacrylates, and cyclic olefin copolymers. The base material in the present embodiment may also be a paper material on which a circular frame is printed with a material containing a cyclic olefin copolymer and a plastic component. The compound according to the first embodiment can be applied to the flow path or the circular frame to retain the compound according to the first embodiment in the frame and detect hydrogen sulfide on the base material with high sensitivity. The region within the circular frame may be a hydrogen sulfide sensing region. In the structural body according to the present embodiment, the compound according to the first embodiment applied to the base material is easily released into the aqueous biological sample, or the aqueous biological sample permeates easily into the base material to which the compound is applied. A material for detecting hydrogen sulfide with low water solubility is therefore strongly adsorbed on the base material by hydrophobic interaction, is rarely brought into contact with hydrogen sulfide, and has lower detection sensitivity. By contrast, the compound according to the present embodiment has high water solubility, is released in a large amount from the base material, or is weakly adsorbed on the base material, easily comes into contact with hydrogen sulfide, and has a smaller decrease in detection sensitivity. Due to the high water solubility of the compound, the structural body according to the present embodiment can detect hydrogen sulfide on the base material with high sensitivity.

One Example of Structural Body

FIGURE illustrates an example of the structural body according to the present embodiment. In the FIGURE, a structural body 101 for detecting hydrogen sulfide includes a hydrogen sulfide detecting material (the compound according to the first embodiment) 102 and a base material 103. If necessary, the structural body 101 may include a supporting member 104.

The addition of a biological sample 105 causes the detecting material 102 adsorbed on the base material 103 to be released from the base material into the specimen or to permeate into the specimen, thereby mixing the detecting material 102 with the aqueous specimen (biological sample). In the presence of hydrogen sulfide, the detecting material 102 on the base material or in the aqueous specimen reacts with the hydrogen sulfide and separates into a xanthene colorant 106 and Dye 107. Hydrogen sulfide can be identified by measuring the fluorescence intensity or luminance in the aqueous specimen or on the base material.

The structural body illustrated in the FIGURE is only an example, and the present disclosure is not limited thereto.

Alternatively, the structural body 101 may be immersed in a solution containing hydrogen sulfide. The xanthene colorant 106 or the Dye 107 separated by hydrogen sulfide is dissolved in the solution. Hydrogen sulfide can also be identified by observing the amount of coloring of the xanthene colorant or Dye dissolved in the solution. The term "the amount of coloring", as used herein, refers to the signal intensity of color intensity or fluorescence intensity.

Use

The structural body according to the present embodiment includes the compound according to the first embodiment and can therefore detect hydrogen sulfide. An enzyme that generates hydrogen sulfide from a metabolite to be detected serving as a substrate may be provided on the base material. For example, homocysteine α,γ-lyase can be used as an enzyme to detect homocysteine. The amount of analyte to be detected can be determined by detecting hydrogen sulfide as a product of an enzymatic reaction. An analyte to be detected can also be detected by using an aqueous specimen to which an enzyme is added in advance to generate hydrogen sulfide from the analyte to be detected. The analyte to be detected may be an enzyme. More specifically, a substrate for an enzyme to be detected can be contained to detect the enzyme.

Enzyme

The enzyme in the present embodiment may be, but is not limited to, at least a member selected the group consisting of cystathionine γ-lyase, 3-mercaptopyruvate sulfurtransferase, thiosulfate reductase, methanethiol oxidase, sulfhydrogenase, sulfur oxygenase/reductase, methylated-thiol-coenzyme M methyltransferase, O-phosphoserine sulfhydrylase, carbon disulfide hydrolase, carbonyl sulfide hydrolase, homocysteine desulfhydrase (homocysteine α,γ-lyase), L-3-cyanoalanine synthase, D-cysteine desulfhydrase. L-cysteine desulfhydrase, L-methionine γ-lyase, and cystathionine β-synthase.

Third Embodiment

Detection Device

A detection device according to a third embodiment of the present disclosure includes a blood cell separation membrane on the base material of the structural body according to the second embodiment. The blood cell separation membrane enables the detection of hydrogen sulfide in the blood. Furthermore, as in the second embodiment, homocysteine α,γ-lyase on the base material can detect homocysteine in the blood.

Fourth Embodiment

A microchannel device according to a fourth embodiment of the present disclosure includes the base material and the compound according to the first embodiment. The base material includes a sensing region in which the compound according to the first embodiment is applied to the base material, a blood droplet region in which a blood cell separation membrane is located on the base material, and a flow path through which plasma or serum can move from the blood droplet region to the sensing region.

Flow Path

The flow path in the present embodiment can be a developing flow path through which plasma or serum can move by capillarity.

In the present embodiment, the base material may be a paper material having a dumbbell-shaped frame printed thereon with a material containing a cyclic olefin copolymer and a plastic component, and the sensing region and the blood droplet region may be located at each end of the dumbbell shape.

Fifth Embodiment

A detection method according to a fifth embodiment of the present disclosure includes a contact step of bringing a dye for detecting hydrogen sulfide into contact with a biological sample and a measurement step of measuring the amount of coloring or fluorescence produced by the contact step. The dye for detecting hydrogen sulfide may be the compound according to the first embodiment.

In the present embodiment, a solid containing a dye for detecting hydrogen sulfide or a solution in which the solid is dispersed may be brought into contact with an aqueous specimen, such as a biological sample, that possibly contains hydrogen sulfide.

The sensing region of the device may be immersed in a biological sample, to which an enzyme for generating hydrogen sulfide is added, in a container to come into contact with the biological sample. Alternatively, a biological sample may be developed on the base material by utilizing capillarity as in paper chromatography to come into contact with the sensing region. The enzyme may be applied to the base material in advance.

In accordance with such a method, after the biological sample is in contact with the sensing region of the base material for a certain period, the amount of change in the signal intensity of color intensity or fluorescence intensity of the sensing region is measured by visual observation or with a reflection densitometer or a fluorescence spectrodensitometer. Thus, the amount of analyte to be detected can be calculated.

A small amount of analyte to be detected causes a small amount of change in the sensing region. A large amount of analyte to be detected causes a large amount of change in the sensing region. The amount of change may also be determined from the coloring intensity in the sensing region or from the fluorescence intensity in the sensing region due to ultraviolet radiation of an ultraviolet lamp or visible light irradiation.

The fourth embodiment of the present disclosure provides a structural body for detecting hydrogen sulfide, which includes the compound according to the first embodiment, the base material, and an enzyme for generating hydrogen sulfide from a metabolite to be detected serving as a substrate.

Sixth Embodiment

Detection Kit

A detection kit according to a sixth embodiment of the present disclosure includes the compound according to the first embodiment or a solution containing the compound, and the base material according to the second embodiment. The detection kit according to the present embodiment can include the base material and a separate container that contains the compound or the solution containing the compound. To detect hydrogen sulfide, the compound is applied to the base material. The amount and concentration of hydrogen sulfide can be measured by dropping a biological sample possibly containing hydrogen sulfide directly onto the coated base material (also referred to as a structural body). A separate container may also be provided for allowing the biological sample to permeate into the structural body. The separate container enables the biological sample to permeate uniformly into the structural body.

The solid enzyme or an aqueous solution containing the enzyme may be contained in a separate container in advance. The biological sample can be added to the container simultaneously with permeation into the structural body. Alternatively, the biological sample can be added to the container and is left for a certain period, and after hydrogen sulfide is generated the biological sample is allowed to permeate into the structural body.

The detection kit according to the present embodiment may include a color sample of hue, brightness, or color saturation to observe the color (fluorescence) change of the structural body depending on the amount or concentration of hydrogen sulfide or metabolite. It may be printed on a paper, plastic plate, or the like. The amount or concentration of hydrogen sulfide or metabolite in the biological sample may also be semi-quantitatively determined by visual observation comparing the color after the change of the structural body with the color sample.

The detection kit according to the present embodiment may include a separate LED light, particularly an LED lamp that emits light in the wavelength range of 365 to 500 nm. A fluorescence change in the sensing region can be visually observed by irradiating the sensing region with light of the LED light as excited light. It is also possible to acquire image data of the sensing region with a compact digital camera or using a camera function of a smartphone and to use an application to measure a color or fluorescence change of the sensing region as an intensity value. Thus, the amount or concentration of hydrogen sulfide or metabolite in the biological sample can be quantitatively determined.

The detection kit according to the present embodiment may include a long-pass filter and preferably has a cut-on wavelength range of 400 to 650 nm. It is also possible to selectively detect only fluorescence by observing or detecting a fluorescence change in the sensing region through a long-pass filter to cut scattering and reflection of excited light. Furthermore, a color cellophane with low excited light transmittance and high fluorescence transmittance may also be used.

The detection kit according to the present embodiment may include a small chamber into which a biological sample, the compound according to the first embodiment, or the structural body according to the second embodiment can be added or inserted. The detection kit according to the present embodiment can be a small chamber with an internal structure for blocking external light, such as sunlight or fluorescent light. This is because only fluorescence can be selectively detected without influence of external light. The small chamber may be integrated with an LED light or a long-pass filter and can have a window through which the inside of the small chamber can be viewed from the outside by visual observation or using a compact digital camera, a camera function of a smartphone, or the like. Furthermore, the small chamber can have a holder function to mount a compact digital camera or a smart phone.

EXEMPLARY EMBODIMENTS

Although the present disclosure is further described in the following exemplary embodiments, the present disclosure is not limited to these exemplary embodiments without departing from the gist of the present disclosure.

<Identification of Compound>

Synthesized compounds (dyes) described below were identified with a $^1$H-NMR measurement apparatus (Bruker Avance 500, manufactured by Bruker, resonant frequency: 500 MHz).

Production Example 1 Synthesis of Compound 1-1

3.11 g of 3-[[(tert-butoxy)carbonyl]amino]propyl 2-cyanoacetate synthesized with reference to Org Biomol Chem. 2011, 9, pp. 3530-3540 (Non Patent Literature 3) was added dropwise to 30 mL of tetrahydrofuran in which 2.15 g of tert-butyl 2-formylbenzoate synthesized with reference to Chem. Commun. 2019, 55, pp. 13610-13613 (Non Patent Literature 2) was dissolved. After 2 mL of diazabicycloundecene was added dropwise, the mixture was stirred overnight at room temperature. After the solvent was distilled off, the mixture was purified by silica gel column chromatography. Thus, 1.60 g of a colorless oil was prepared.

Production Example 2 Synthesis of Compound 1-2

0.89 g of the compound 1-1 was added to 12 mL of a liquid mixture of trifluoroacetic acid and dichloromethane (v/v=1/1), and the mixture was stirred at room temperature for 3 hours. After the solvent was distilled off, 25 mL of N,N-dimethylformamide and 2 mL of triethylamine were added to the mixture. After 0.07 g of dimethylaminopyridine and 0.76 g of N-succinimidyl 4-[4-(Dimethylamino)phenylazo]benzoate (manufactured by Tokyo Chemical Industry Co., Ltd.) were added, the mixture was stirred overnight at room temperature. After the solvent was distilled off, the mixture was purified by silica gel column chromatography. Thus, 0.60 g of a red solid was prepared.

Production Example 3 Synthesis of Compound 1

280 mg of the compound 1-2 and 336 mg of water-soluble carbodiimide were added to 20 mL of N,N-dimethylformamide, and the mixture was stirred at room temperature for 1 hour. 73 mg of dimethylaminopyridine (manufactured by Tokyo Chemical Industry Co., Ltd.) and 392 mg of fluorescein (manufactured by Tokyo Chemical Industry Co., Ltd.) were added to the mixture, and the mixture was stirred overnight at room temperature. After the solvent was distilled off, the mixture was purified by silica gel column chromatography. Thus, 19 mg of a red solid was prepared. $^1$H-NMR (CD$_3$OD) (ppm): 9.02 (s, 1H), 8.32 (m, 1H), 8.02-7.75 (m, 9H), 7.68-7.60 (m, 2H), 7.20-7.11 (m, 2H), 6.87-6.55 (m, 8H), 4.48-4.42 (m, 2H), 3.66-3.63 (m, 2H), 3.10 (s, 6H), 2.12-2.10 (m, 2H)

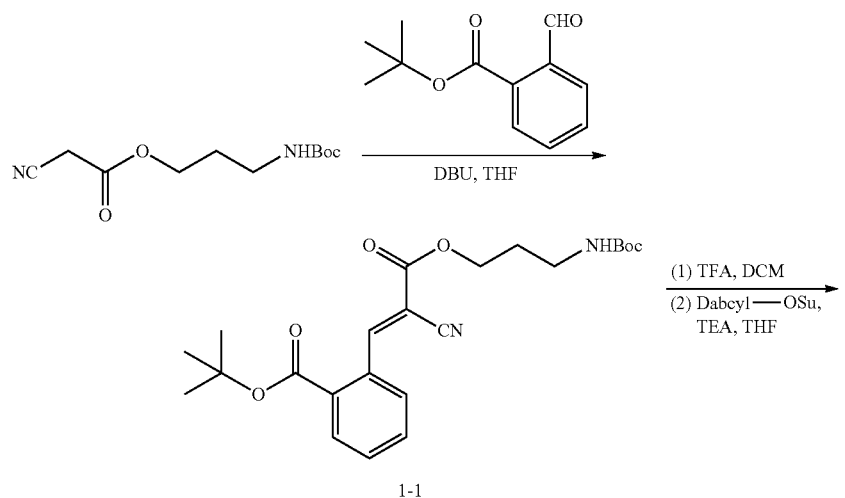
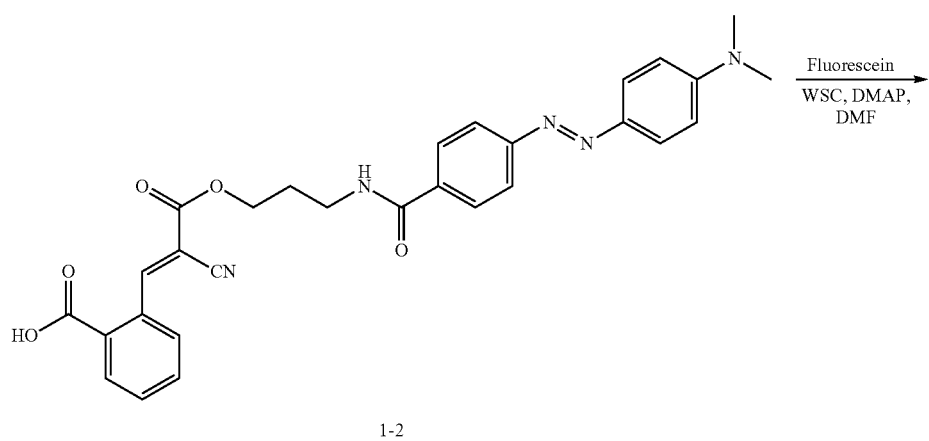
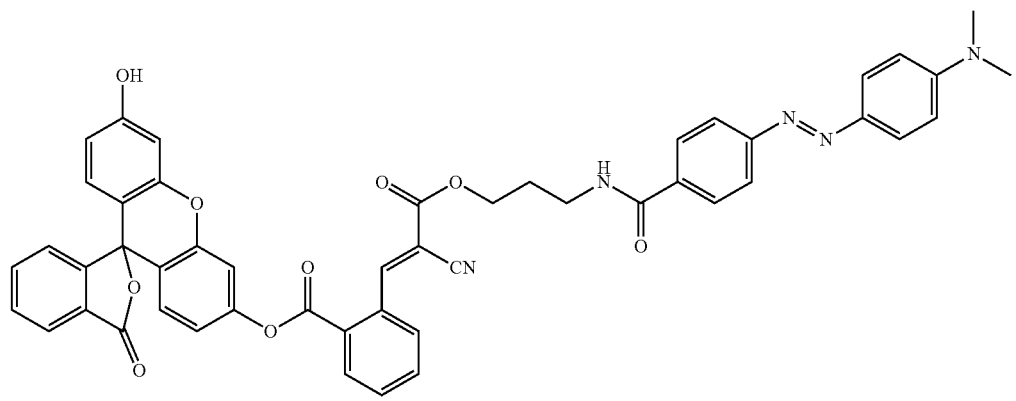

Production Example 4 Synthesis of Compound 2

Referring to Non Patent Literature 1, 64 mg of a white solid was prepared.

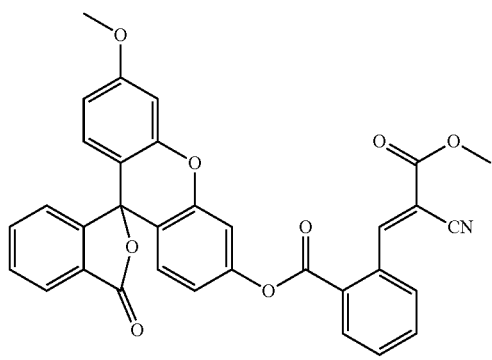

2

Production Example 5 Synthesis of Compound 3-1

79 mg of fluorescein isothiocyanate, isomer I (manufactured by Sigma-Aldrich Corporation), 39 mg of glycine tert-butyl ester hydrochloride (manufactured by Tokyo Chemical Industry Co., Ltd.), and 0.1 mL of triethylamine were added to 5 mL of N,N-dimethylformamide, and the mixture was stirred at room temperature for 3 hours. After the solvent was distilled off, the mixture was purified by silica gel column chromatography. Thus, 80 mg of an orange solid was prepared.

Production Example 6 Synthesis of Compound 3-2

20 mg of the compound 1-2, 25 mg of water-soluble carbodiimide, and 5 mg of dimethylaminopyridine were added to 5 mL of N,N-dimethylformamide, and the mixture was stirred at room temperature for 1 hour. 46 mg of the compound 3-1 was added to the mixture, and the mixture was stirred overnight at room temperature. After the solvent was distilled off, ethyl acetate was added to the mixture, and the mixture was washed with water. The ethyl acetate phase was collected, was dried over sodium sulfate, and was filtered. After the solvent of the filtrate was distilled off, the residue was purified by silica gel column chromatography. Thus, 10 mg of a red solid was prepared.

Production Example 7 Synthesis of Compound 3

Trifluoroacetic acid (2 mL) was added to 10 mg of the compound 3-2, and the mixture was stirred at room temperature for 3 hours. The solvent was distilled off. Thus, 10 mg of a red solid was prepared. $^1$H-NMR (CD$_3$OD/CDCl$_3$=1/1) (ppm): 9.02 (s, 1H), 7.96-7.84 (m, 11H), 7.35-7.32 (m, 1H), 7.20-7.15 (m, 1H), 6.93-6.73 (m, 8H), 4.43-4.41 (m, 4H), 3.73-3.69 (m, 2H), 3.16 (s, 6H), 2.14-2.11 (m, 2H).

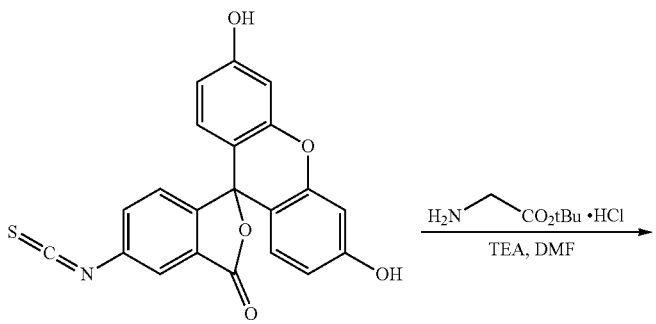

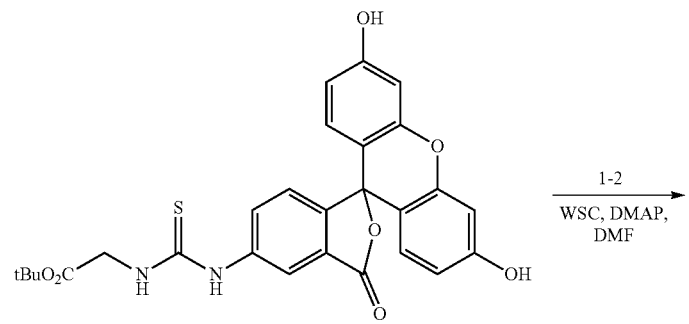

3-1

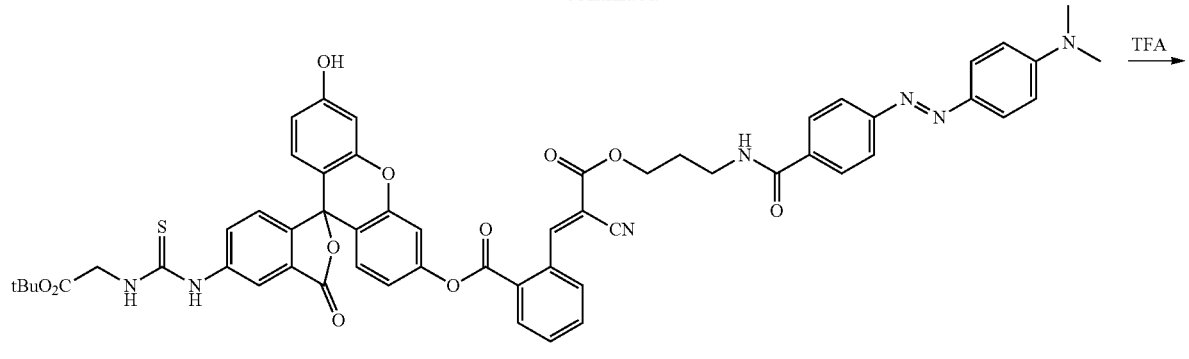

3-2

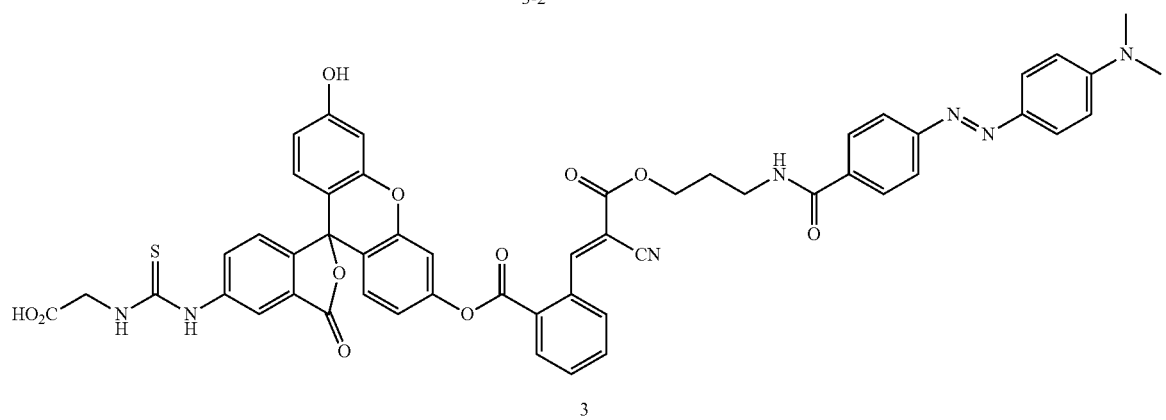

3

Production Example 8 Synthesis of Compound 4

19 mg of the compound 1-2, 23 mg of water-soluble carbodiimide, and 5 mg of dimethylaminopyridine were added to 5 mL of N,N-dimethylformamide, and the mixture was stirred at room temperature for 30 minutes. 32 mg of 2',7'-dichlorofluorescein (manufactured by Tokyo Chemical Industry Co., Ltd.) was added to the mixture, and the mixture was stirred overnight at room temperature. After the solvent was distilled off, the mixture was purified by silica gel column chromatography. Thus, 20 mg of a red solid was prepared. $^1$H-NMR (CDCl$_3$) (ppm): 9.04 (s, 1H), 8.08-7.82 (m, 12H), 7.75-7.66 (m, 2H), 7.20-7.11 (m, 2H), 6.77-6.67 (m, 6H), 4.49-4.42 (m, 2H), 3.66-3.62 (m, 2H), 3.11 (s, 6H), 2.14-2.11 (m, 2H).

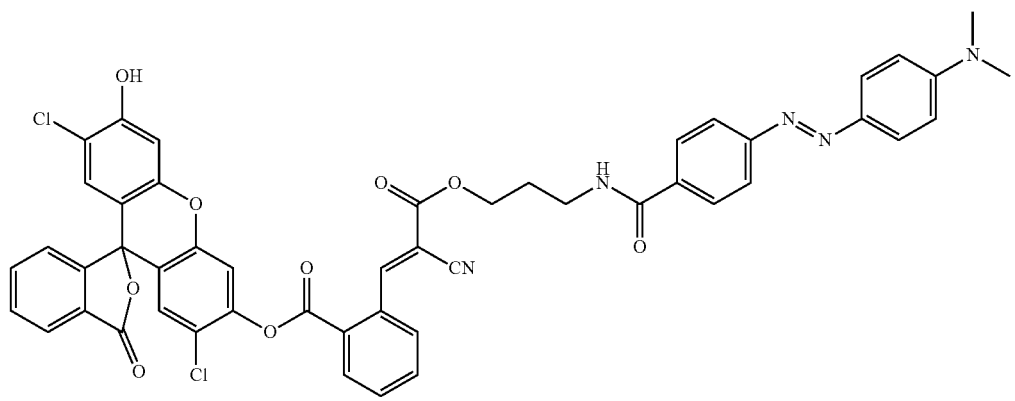

4

Production Example 9 Synthesis of Compound 5-1

70 mg of fluorescein isothiocyanate, isomer I (manufactured by Sigma-Aldrich Corporation), 38 mg of 3,6,9,12-tetraoxadecane amine (manufactured by Tokyo Chemical Industry Co., Ltd.), and 0.1 mL of triethylamine were added to 1 mL of N,N-dimethylformamide, and the mixture was stirred overnight at room temperature. After the solvent was distilled off, the mixture was purified by silica gel column chromatography. Thus, 95 mg of an orange solid was prepared.

Production Example 10 Synthesis of Compound 5

23 mg of the compound 1-2, 25 mg of water-soluble carbodiimide, and 6 mg of dimethylaminopyridine were added to 3 mL of N,N-dimethylformamide, and the mixture was stirred at room temperature for 1 hour. 47 mg of the compound 5-1 was added to the mixture, and the mixture was stirred overnight at room temperature. After the solvent was distilled off, the mixture was purified by silica gel column chromatography. Thus, 11 mg of a red solid was prepared. $^1$H-NMR (CDCl$_3$) (ppm): 9.01 (s, 1H), 8.78 (br, 1H), 8.32-8.31 (m, 1H), 8.07 (br, 1H), 7.99-7.97 (m, 1H), 7.90-7.77 (m, 9H), 7.10-7.05 (m, 3H), 6.87-6.85 (m, 1H), 6.77-6.66 (m, 6H), 6.57-6.55 (m, 2H), 4.42 (t, 2H, J=5.5 Hz), 3.88-3.83 (m, 2H), 3.72-3.58 (m, 16H), 3.32 (s, 3H), 3.10 (s, 6H), 2.12-2.08 (m, 2H).

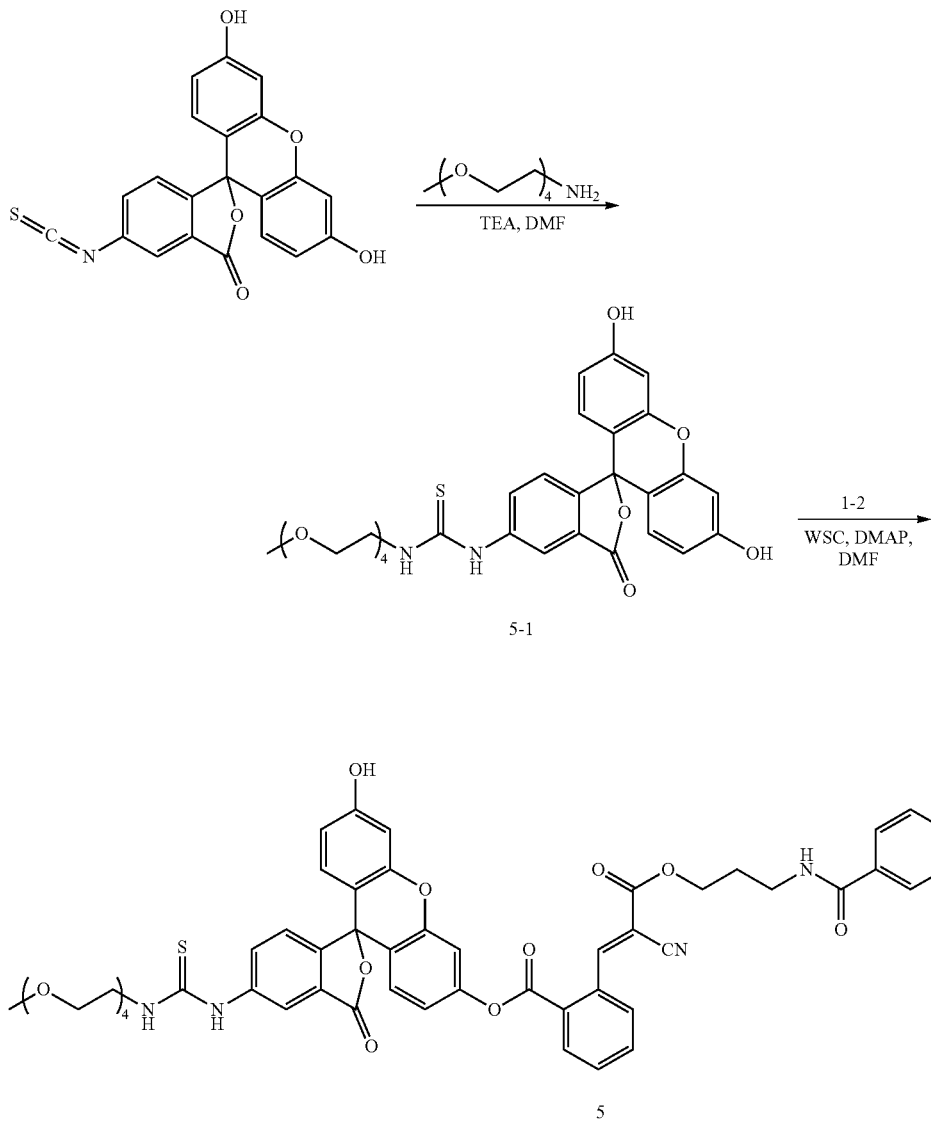

Production Example 11 Synthesis of Compound 6

12 mg of the compound 1-2, 16 mg of water-soluble carbodiimide, and 3 mg of dimethylaminopyridine were added to 1 mL of N,N-dimethylformamide, and the mixture was stirred at room temperature for 30 minutes. 10 mg of 2',7'-difluorofluorescein (manufactured by Thermo Fisher Scientific Inc.) was added to the mixture, and the mixture was stirred overnight at room temperature. After the solvent was distilled off, the mixture was purified by silica gel column chromatography. Thus, 2 mg of a red solid was prepared.

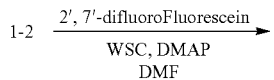

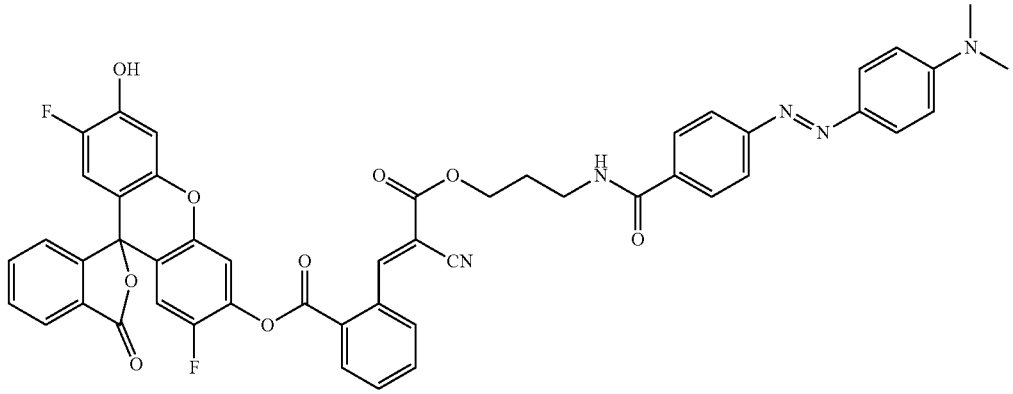

Production Example 12 Synthesis of Compound 7

27 mg of the compound 1-2, 30 mg of water-soluble carbodiimide, and 7 mg of dimethylaminopyridine were added to 2 mL of N,N-dimethylformamide, and the mixture was stirred at room temperature for 2 hours. 48 mg of 3,4,5,6-tetrachlorofluorescein (manufactured by Tokyo Chemical Industry Co., Ltd.) was added to the mixture, and the mixture was stirred overnight at room temperature. After the solvent was distilled off, the mixture was purified by silica gel column chromatography. Thus, 9 mg of a red solid was prepared. $^{1}$H-NMR (CDCl$_3$) (ppm): 9.04 (s, 1H), 8.58 (br, 1H), 7.90-7.85 (m, 7H), 7.83 (m, 1H), 7.78 (m, 1H), 7.13-7.12 (m, 1H), 6.98-6.94 (m, 1H), 6.90-6.88 (m, 1H), 6.77-6.71 (m, 4H), 6.62-6.60 (m, 1H), 6.57-6.54 (m, 1H), 5.76 (br, 1H), 4.45 (t, 2H, J=6.0 Hz), 3.68-3.64 (m, 2H), 3.11 (s, 6H), 2.15-2.10 (m, 2H).

Exemplary Embodiment 1

The compound 1 was added to 1× phosphate-buffered saline (3 mL, pH 7.4) at a concentration of 5 μM. The fluorescence intensity of the solution was immediately measured with a fluorescence spectrophotometer F-4500 (manufactured by Hitachi High-Technologies Corporation). Sodium sulfide serving as a hydrogen sulfide donor was then added to the solution at 0.2 mM. After standing for 10 minutes, the fluorescence intensity of the solution was measured. The fluorescence intensity before the addition of sodium sulfide was denoted as $F_1$, and the fluorescence intensity 10 minutes after the addition of sodium sulfide was denoted as $F_2$. The amount of change in fluorescence intensity (ΔF) due to the addition of sodium sulfide was calculated using the formula $F_2-F_1$. The concentration of sodium sulfide was changed to 0 mM, and the amount of change in

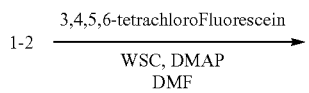

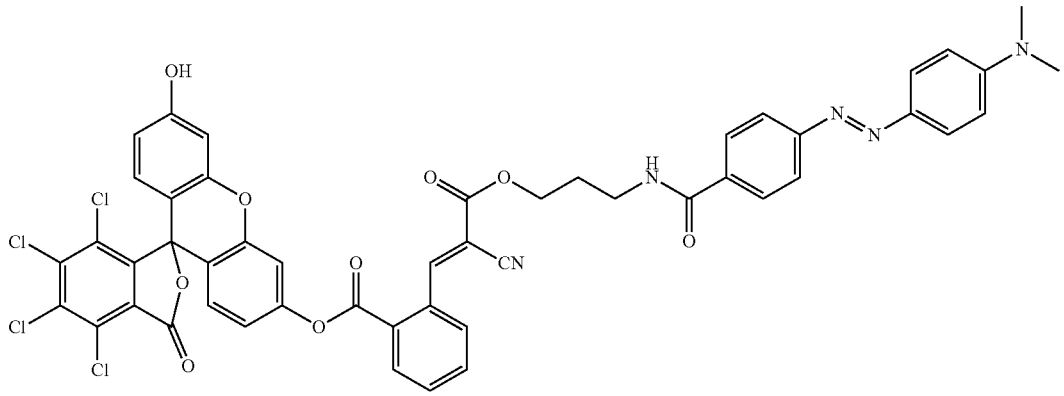

fluorescence intensity ($\Delta F_0$) of the solution was calculated in the same manner. The difference in the amount of change in fluorescence intensity ($\Delta F - \Delta F_0$) in the presence or absence of sodium sulfide was calculated. Table 1 shows the calculated values.

Exemplary Embodiment 2

Exemplary embodiment 2 was performed in the same manner as in Exemplary embodiment 1 except that the compound 1 was replaced with the compound 3.

Exemplary Embodiment 3

Exemplary embodiment 3 was performed in the same manner as in Exemplary embodiment 1 except that the compound 1 was replaced with the compound 5.

Comparative Example 1

Comparative example 1 was performed in the same manner as in Exemplary embodiment 1 except that the compound 1 was replaced with the compound 2.

Comparative Example 2

Comparative example 2 was performed in the same manner as in Exemplary embodiment 1 except that the compound 1 was replaced with the compound 4.

Comparative Example 3

Comparative example 3 was performed in the same manner as in Exemplary embodiment 1 except that the compound 1 was replaced with the compound 6.

Comparative Example 4

Comparative example 4 was performed in the same manner as in Exemplary embodiment 1 except that the compound 1 was replaced with the compound 7.

[Sensitivity]

The evaluation is based on the following criteria in the exemplary embodiments of the present disclosure. A to C are acceptable levels, and D is an unacceptable level. A larger $\Delta F - \Delta F_0$ indicates that hydrogen sulfide is detected with higher sensitivity.

A: $\Delta F - \Delta F_0$ is 40 or more.
B: $\Delta F - \Delta F_0$ is 25 or more and less than 40.
C: $\Delta F - \Delta F_0$ is 15 or more and less than 25.
D: $\Delta F - \Delta F_0$ is less than 15.

Table 1 shows the amounts of change in fluorescence intensity $\Delta F$ and $\Delta F_0$ of the solution in each of the exemplary embodiments and the comparative examples, the difference in the amount of change in fluorescence intensity $\Delta F - \Delta F_0$ in the presence or absence of sodium sulfide, and the evaluation results.

It was found that hydrogen sulfide can be detected with high sensitivity using the compounds according to the exemplary embodiments of the present disclosure.

TABLE 1

| | Compound No. | $\Delta F$ (0.2 mM sodium sulfide) | $\Delta F_0$ (0 mM sodium sulfide) | $\Delta F - \Delta F_0$ | Sensitivity |
|---|---|---|---|---|---|
| Exemplary embodiment 1 | 1 | 42.8 | 1.1 | 41.7 | A |
| Exemplary embodiment 2 | 3 | 36.9 | 6.8 | 30.1 | B |
| Exemplary embodiment 3 | 5 | 42.3 | 1.2 | 41.1 | A |
| Comparative example 1 | 2 | 11.4 | −0.4 | 11.8 | D |
| Comparative example 2 | 4 | 10.3 | 4.9 | 5.4 | D |
| Comparative example 3 | 6 | 34.0 | 13.3 | 20.7 | C |
| Comparative example 4 | 7 | 8.8 | 2.2 | 6.5 | D |

A novel compound according to the present disclosure can detect hydrogen sulfide in an aqueous specimen, such as a biological sample, with high sensitivity.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2020-196001 filed Nov. 26, 2020, which is hereby incorporated by reference herein in its entirety.

What is claimed is:

1. A compound represented by formula 1:

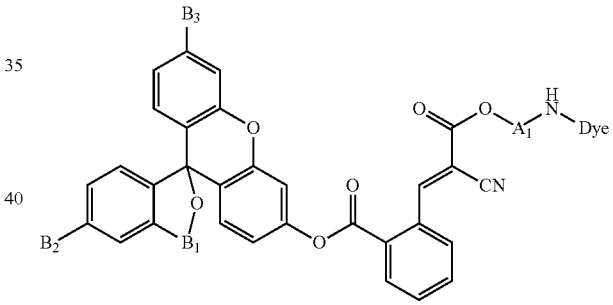

(formula 1)

wherein
Dye denotes an optical absorber with optical absorption in a wavelength range of 350 to 700 nm and with a highest molecular absorption coefficient of $10^4$ $M^{-1}$ $cm^{-1}$ or more,
$A_1$ denotes a substituted or unsubstituted alkylene or alkoxy group having 3 to 12 carbon atoms,
$B_1$ denotes a member selected from the group consisting of —C(=O)—, —S(=O)$_2$—, and —CH$_2$—,
$B_2$ denotes a member selected from the group consisting of —H, —NHC(=S)NH—(CH$_2$CH$_2$O)$_n$—CH$_3$, and —NHC(=S) amino acids, wherein n denotes an integer in the range of 1 to 25, and
$B_3$ denotes a member selected from the group consisting of —OH, —NH$_2$, —NHCH$_3$, —NHCH$_2$CH$_3$, —N(CH$_3$)$_2$, and —N(CH$_2$CH$_3$)$_2$.

2. The compound according to claim 1, wherein $B_3$ in the formula 1 denotes —OH.

3. The compound according to claim 1, wherein $B_1$ in the formula 1 denotes —C(=O)—.

4. The compound according to claim 1, wherein $B_2$ in the formula 1 denotes a member selected from the group consisting of —H, —NHC(=S)NH—(CH$_2$CH$_2$O)$_n$—CH$_3$, and —NHC(=S)NH—CH$_2$—COOH.

5. The compound according to claim 1, wherein A$_1$ in the formula 1 denotes an alkylene group having 3 carbon atoms.

6. The compound according to claim 1, wherein Dye in the formula 1 is represented by the formula 2:

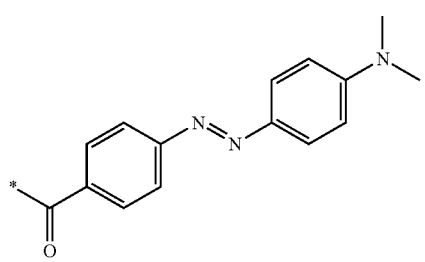

(formula 2)

wherein * denotes the position of N of NH in the formula 1.

7. A structural body comprising:
a base material; and
the compound according to claim 1 on the base material.

8. The structural body according to claim 7, further comprising an enzyme on the base material, the enzyme generating hydrogen sulfide from a metabolite to be detected serving as a substrate.

9. The structural body according to claim 8, wherein the enzyme is homocysteine α,γ-lyase or L-methionine γ-lyase.

10. A detection device configured to detect hydrogen sulfide in blood, comprising a blood cell separation membrane on the structural body according to claim 7.

11. A detection device configured to detect homocysteine, L-cysteine, D-cysteine, L-methionine, cystathionine, methanethiol, thiosulfate, carbon disulfide, or 3-mercaptopyruvate in blood, comprising a blood cell separation membrane on the structural body according to claim 8.

12. The detection device according to claim 10, wherein the base material includes a paper material having a circular frame printed thereon with a material containing a cyclic olefin copolymer and a plastic component.

13. A microchannel device comprising:
a base material; and
the compound according to claim 1 on the base material, wherein the base material includes a sensing region in which the compound is applied to the base material, a blood droplet region in which a blood cell separation membrane is located on the base material, and a flow path through which plasma or serum can move from the blood droplet region to the sensing region.

14. The microchannel device according to claim 13, wherein the sensing region is located on the base material coated with homocysteine α,γ-lyase or L-methionine γ-lyase.

15. The microchannel device according to claim 13, wherein the blood droplet region is located on a base material coated with homocysteine α,γ-lyase or L-methionine γ-lyase.

16. The microchannel device according to claim 13, wherein the base material includes a paper material having a dumbbell-shaped frame printed thereon with a material containing a cyclic olefin copolymer and a plastic component, and the sensing region and the blood droplet region are located at each end of the dumbbell shape.

17. A detection method comprising the steps of:
bringing the compound according to claim 1 into contact with a biological sample; and
measuring the amount of coloring or fluorescence produced by the contact step.

18. The detection method according to claim 17, wherein the contact step includes the step of mixing the biological sample with homocysteine α,γ-lyase or L-methionine γ-lyase to generate hydrogen sulfide.

19. The detection method according to claim 18, wherein the contact step includes the step of bringing a base material coated with the compound and with the homocysteine α,γ-lyase or L-methionine γ-lyase into contact with a biological sample.

20. The structural body according to claim 8, wherein the enzyme is at least a member selected from the group consisting of cystathionine γ-lyase, 3-mercaptopyruvate sulfurtransferase, thiosulfate reductase, methanethiol oxidase, sulfhydrogenase, sulfur oxygenase/reductase, methylated-thiol-coenzyme M methyltransferase, O-phosphoserine sulfhydrylase, carbon disulfide hydrolase, carbonyl sulfide hydrolase, homocysteine desulfhydrase (homocysteine α,γ-lyase), L-3-cyanoalanine synthase, D-cysteine desulfhydrase, L-cysteine desulfhydrase, L-methionine γ-lyase, and cystathionine β-synthase.

* * * * *